United States Patent [19]

Sagenmüller et al.

[11] Patent Number: 5,792,755
[45] Date of Patent: Aug. 11, 1998

[54] SYNERGISTIC COMBINATIONS OF AMMONIUM SALTS

[75] Inventors: Alfons Sagenmüller, Kelsterbach, Germany; Hans-Herbert Schubert, Tokyo, Japan; Shigeru Uzawa, Chiba, Japan; Kenichi Saito, Mobara, Japan

[73] Assignee: Hoechst Aktiengesellschaft, Frankfurt, Germany

[21] Appl. No.: 374,309

[22] Filed: Jan. 18, 1995

[30] Foreign Application Priority Data

Jan. 20, 1994 [DE] Germany .................. 44 01 542.9

[51] Int. Cl.$^6$ .................. A01N 33/12; A01N 55/00
[52] U.S. Cl. .................. 514/63; 514/643
[58] Field of Search .................. 514/63, 643

[56] References Cited

U.S. PATENT DOCUMENTS

| | | | |
|---|---|---|---|
| 4,844,734 | 7/1989 | Iwasaki et al. | 71/120 |
| 4,888,049 | 12/1989 | Iwasaki et al. | 71/94 |

FOREIGN PATENT DOCUMENTS

| | | |
|---|---|---|
| A-0 387 663 | of 0000 | European Pat. Off. |
| A-0 211 561 | 2/1987 | European Pat. Off. |
| A-0 453 086 | 10/1991 | European Pat. Off. |
| 0 211 561 B1 | 3/1992 | European Pat. Off. |
| 0 302 389 B1 | 12/1993 | European Pat. Off. |
| 61-87687 | 5/1986 | Japan .................. 514/63 |
| 483368 | 4/1938 | United Kingdom .................. 514/643 |
| 648400 | 1/1951 | United Kingdom .................. 514/643 |
| 2 178 739 B | 2/1987 | United Kingdom . |
| 2 187 452 | 9/1987 | United Kingdom . |

OTHER PUBLICATIONS

Cross; C.A., vol. 94, (1981) 94:32,429d.
Database WPI, Derwent Publications Ltd. and Japanese Application JP-A-01 203 304, Aug. 16, 1989.
Database WPI, Derwent Publications Ltd., AN86-116639 (1986).
Database WPI, Derwent Publications Ltd., AN92-021495 (1991).
Chemical Abstracts, vol. 107, No. 22, No. 220735h (1987).
Chemical Abstracts, vol. 94, No. 20, No. 158558p (1981).

*Primary Examiner*—Allen J. Robinson
*Attorney, Agent, or Firm*—Curtis, Morris & Safford, P.C.

[57] ABSTRACT

The invention relates to insecticidal compositions which comprise

A) inorganic or organic ammonium salts of the formula I

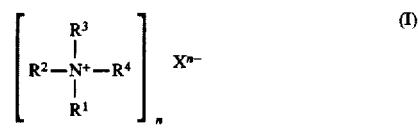

in combination with at least one compound from the group consisting of the compounds silafluofen (4-ethoxyphenyl-[3-(4-fluoro-3-phenoxyphenyl)propyl]dimethylsilane), MTI-723, imidacloprid, ethofenprox (Trebon, MTI-500, (2-(4- ethoxyphenyl)-2-methylpropyl-3-phenoxybenzyl ether), PP 682 (ICI-A5682), T1304, natural or synthetic pyrethroids and phosphorothioates.

7 Claims, No Drawings

SYNERGISTIC COMBINATIONS OF AMMONIUM SALTS

The insecticides of a range of structural classes which have recently been found have a good insecticidal activity and act against insects which destroy materials. There is nevertheless a demand for compositions which have the same action even at low application rates.

There have now been found novel combinations of ammonium salts and insecticides which have surprisingly powerful synergistic effects in the control of insects which destroy materials.

The present invention therefore relates to insecticidal compositions comprising

A) inorganic or organic ammonium salts of the formula $$\left[\begin{array}{c} R^3 \\ | \\ R^2-N^+-R^4 \\ | \\ R^1 \end{array}\right]_n X^{n-} \quad (I)$$

in which $R^1$–$R^4$ are identical or different and independently of one another are hydrogen or an organic substituent having up to 18 C atoms which is bonded via a C–N bond, at least one of the radicals $R^1$–$R^4$ being other than hydrogen and $X^{n-}$ being the anion of an inorganic or organic n-basic acid, and n being 1, 2 or 3, in combination with at least one compound from amongst the group consisting of the compounds B) silafluofen (4-ethoxyphenyl[3-(4-fluoro-3-phenoxyphenyl) propyl]dimethylsilane, formula II),

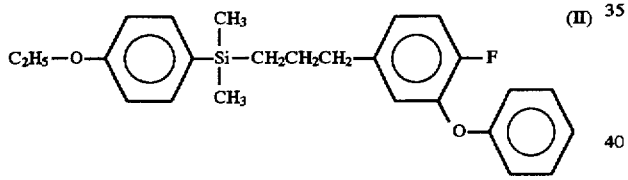

C) MTI-732 (formula III),

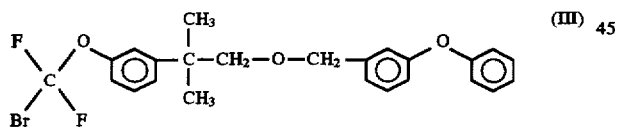

D) imidacloprid (formula IV),

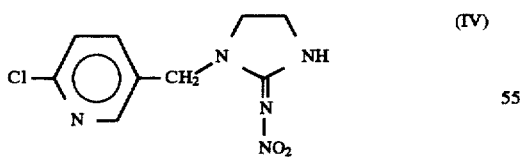

E) ethofenprox (Trebon, MTI-500, (2-(4-ethoxyphenyl) -2-methylpropyl 3-phenoxybenzyl ether, formula V),

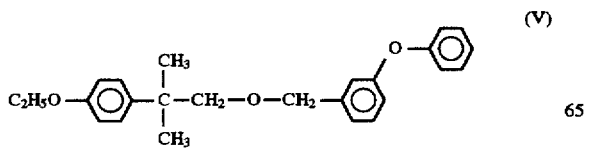

F) PP 682 (ICI-A5682, formula VI),

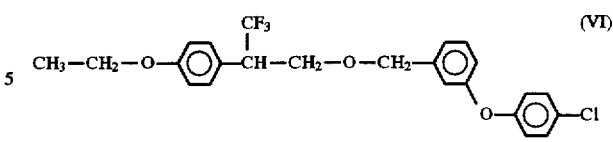

G) TI304 (formula VII),

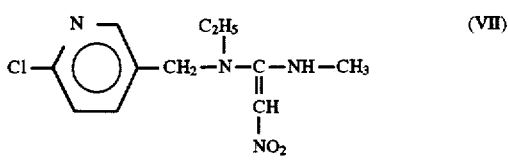

H) natural or synthetic pyrethroids and

I) phosphoric acid esters.

The compounds of type A are preferably ammonium salts wherein $R^1$ to $R^4$ are identical or different and independently of one another are hydrogen, $(C_1-C_{18})$-alkyl; $(C_7-C_{13})$-aralkyl, such as benzyl; $(C_1-C_6)$-alkoxy-$(C_1-C_{12})$-alkyl; $[-CH_2-CH_2-O]_x$ —H or $[-CH(CH_3)-CH_2-O]_x$—H and x=1, 2 or 3.

Particularly preferred are salts in which $R^1$ and $R^2$ are in each case $(C_1-C_4)$-alkyl, in particular methyl, and $R^3$ and $R^4$ are in each case $(C_8-C_{12})$-alkyl, in particular decyl or benzyl.

Preferred anions $X^{n-}$ are $Cl^-$, $Br^-$, $SO_4^{2-}$, $HSO_4^-$, $PO_4^{3-}$, $HPO_4^{2-}$, $H_2PO_4^-$, $CH_3COO^-$, $COO_2^{2-}$, $SCN^-$, in particular $Cl^-$.

In the compounds of type A, the following compound groups are of particular interest:

1) Primary ammonium salts such as, for example, stearylammonium acetate (Genamin®-SH 500 A), oleylammonium acetate (Genamin®-OL 500 A), tallow fatty amine acetate (Genamin®-TA 500 A), coconut fatty amine oleate (Genamin®-CC 500 E), coconut fatty amine acetate (Genamin®-CC 500 A) and tallow fatty propylenediaminoacetate (Genamin®-TAP 500 E).

2) Secondary ammonium salts such as, for example, Pr äpagen® WKL brands (a range of dialkylammonium chlorides).

3) Tertiary ammonium salts such as, for example, cetyldimethylammonium chloride or oleyldimethylammonium chloride.

4) Quaternary ammonium salts such as, for example, hexadecyltrimethylammonium chloride (Dodigen 1383®),
hexadecyltrimethylammonium chloride (Dodigen 2544®),
soya alkyltrimethylammonium chloride (Dodigen 5594®),
coconut alkyldimethylbenzylammonium chloride (Dodigen 226®),
coconut alkyldimethylbenzylammonium chloride (Dodigen 5462®),
coconut alkyl-2,4-dichlorobenzyldimethylammonium chloride (Dodigen 1509®),
stearyldimethylbenzylammonium chloride (Dodigen 1828®),
di-coconut alkyldimethylammonium chloride (Dodigen 1490®),
distearyldimethylammonium chloride (Pr äpagenWK®), quaternary dialkylammonium chloride (Präpagen WKL®) and di-tallow fatty alkyldimethylammonium chloride (Präpagen WKT®);

Dodigen®, Präpagen® and Genamin®-K brands such as Genamin®-KDM-F (a series of alkyltrimethylammonium chlorides) or distearyldimethylammonium chloride (Genamin®-DSAC) and didecylmethylpolyoxyethylammonium propionate (Dodigen® 3519);

Präpagen® WK 1852, WKL, WKT (a series of di-fatty acid dimethylammonium chlorides), and various benzyltrimethylammonium chlorides of the Dodigen® 1611 and 2809 type.

These primary, secondary, tertiary and quaternary ammonium salts as well as others which are suitable according to the invention are described in McCutcheon's—Emulsifiers & Detergents, (1991), Glen Rock.

The use of the compound Al (Sanisol B-50 ® [alkylbenzyl-dimethylammonium chloride]), of the formula (VIII),

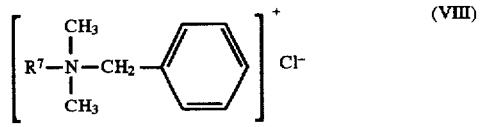

in which $R^7$ is ($C_8$–$C_{18}$)-alkyl is of particular interest.

The compounds of type H are preferably pyrethroids, such as (S) -α-cyano-3-phenoxybenzyl (1R,3R)-3-(2,2-dibromo-vinyl) 2,2-dimethylcyclopropanecarboxylate [delta-methrin], acrinathrin, allethrin, alphamethrin, bioallethrin ((S)-cyclopentenyl isomer), bioresmethrin, cycloprothrin, cyfluthrin, cyhalothrin, cypermethrin, α-cyano-3-phenyl-2-methylbenzyl 2,2-dimethyl-3-(2-chloro-2-trifluoromethylvinyl) -cyclopropanecarboxylate (FMC 54800), fenpropathrin, fenfluthrin, flumethrin, permethrin, resmethrin, fenvalerate or tralomethrin.

Acrinathrin, tralomethrin, permethrin and cypermethrin are preferred pyrethroids; fenvalerate, tralomethrin and deltamethrin are particularly preferred.

The compounds of type I are preferably phosphorothioates such as chlorpyriphos, triazophos and isazophos.

The compositions according to the invention can, besides the ammonium salts, comprise one or more components. Silafluofen and the ammonium salts are commercially available.

The compound ethofenprox (MTI-500, Trebon) is described in "Farm Chemicals Handbook", Willoughby (1991).

The compound MTI-732 is described in DE 3 708 231.
The compound imidacloprid is described in EP 0 192 060.
The compound PP682 (ICI-A5682) is disclosed in GB 2187452, GB 2178739 and in EP 0 211 561.
The compound TI-304 is disclosed in EP 0 302 389 and in EP 0 375 613.

The remaining components are known from "The Pesticide Manual", 9th ed., British Crop Protection Council (1991).

The use of mixtures causing synergistic effects entails substantial economical, but also ecological, advantages.

Synergism is to be understood as meaning the mutually enhancing activity of two or more substances. In the present case, the combined use of two or more compounds has such an effect that the rates of application of the insecticides may be reduced while it is still possible to achieve the same insecticidal activity, or that the same rates of application of the insecticides cause a higher activity than the additive activity to be expected by using the compounds individually. The reduced rates of application apply to both components.

The compositions according to the invention are well tolerated by plants and have a favorable toxicity to warm-blooded species and are particularly preferably suitable for controlling insects which can be found in agriculture, in forests, in the protection of stored products and materials, and in the hygiene sector.

The following fields of application are of particular interest: preventive and curative treatment of wood, and treatment of the soil.

The compositions are active against normally sensitive and resistant species and against all or individual development stages.

The abovementioned pests include:

From the order of the Arachnida, for example, *Scorpio maurus*, *Lactrodectus mactans*.

From the order of the Acarina, for example, *Acarus siro*, *Agras* spp., *Ornithodoros* spp., *Dermanyssus gallinae*, *Eriophyes ribis*, *Phyllocoptruta oleivora*, *Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa*, *Panonychus* spp., *Tetranychus* spp.

From the order of the Isopoda, for example, *Oniscus asellus*, *Armadillidium vulgare* and *Porcellio scaber*.

From the order of the Diplopoda, for example, *Blaniulus guttulatus*.

From the order of the Chilopoda, for example, *Geophilus carpophagus* and *Scutigera* spp.

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Blatta orientalis* and *Periplaneta americana*, *Leucophaea maderae*, *Blatella germanica*, *Acheta domesticus*, *Gryllotalpa* spp., *Locusta migratoria migratorioides*, *Melanoplus differentialis*, *Oxya* spp. and *Schistocerca gregaria*.

From the order of the Dermaptera, for example, *Forficula auricularia*.

From the order of the Anoplura, for example, *Phylloxera vastatrix*, *Pemphigus* spp., *Pediculus humanus corporis*, *Haematopinus* spp. and *Linognathus* spp.

From the order of the Mallophaga, for example, *Trichodectes* spp. and *Damalinea* spp.

From the order of the Thysanoptera, for example, *Hercinothrips femoralis* and *Thrips tabaci*.

From the order of the Heteroptera, for example, *Eurygaster* spp., *Dysdercus intermedius*, *Piesma quadrata*, *Cimex lectularius*, *Rhodnius prolixus*, *Triatoma* spp., *Leptocorisa* spp., *Nezara viridula* and *Scotinophara quadrata*.

From the order of the Homoptera, for example, *Aleurodes brassicae*, *Bemisia tabaci*, *Trialeurodes vaporariorum*, *Aphis gossypii*, *Brevicoryne brassicae*, *Cryptomyzus ribis*, *Doralis fabae*, *Doralis pomi*, *Eriosoma lanigerum*, *Hyalopterus arundinis*, *Macrosiphum avenae*, *Myzus* spp., *Phorodon humuli*, *Rhopalosiphum padi*, *Empoasca* spp., *Euscelus bilobatus*, *Nephotettix cincticeps*, *Lecanium corni*, *Saissetia oleae*, *Laodelphax striatellus*, *Nilaparvata lugens*, *Aonidiella aurantii*, *Aspidiotus hederae*, *Pseudococcus* spp., *Psylla* spp. and *Sogatella furcifera*.

From the order of the Lepidoptera, for example, *Pectinophora gossypiella*, *Bupalus piniarius*, *Cheimatobia*

*brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana.* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima, Tortrix viridana* and Cnaphalocrocis medinalis, Chilo spp., *Sesamia inferens,* Tryporyza spp. and *Parnara gutata.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylloides chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., Meligethes aeneus, Ptinus spp., *Niptus hololeucus, Gibbium psylloides,* Tribolium spp., *Tenebrio molitor,* Agriotes spp., Conoderus spp., *Melolontha melolontha, Amphimallon solstitialis, Costelytra zealandica, Lissorhoptrus oryzaephilus* and *Oulema oryzae.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hypobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae, Tipula paludosa,* Hydrellia spp. and *Chlorops oryzae.*

From the order of the Siphonaptera, for example, *Xenopsylla cheopis* and Ceratophyllus spp. From the order of the Arachnida, for example, Scorpio maurus and Latrodectus mactans.

Most of the insects which destroy wood belong to the Coleoptera, Lepidoptera and Isoptera, which include the termites.

The compositions according to the invention are preferably employed against wood-destroying termites such as, for example, Reticulitermes, Coptotermes and Cryptotermes, against representatives of the sub-class of the Cerambycidae such as, for example, *Hylotrupes bajulus* (house longhorn beetle), against representatives of the sub-class of the Anobilidae, such as, for example, *Anobium punctatum* (death-watch beetle), against representatives of the sub-class of the Ipidae, such as, for example, *Xyloterus lineatus* (striped ambrosia beetle), against representatives of the sub-class of the Platypodidae, such as, for example, *Platypus cylindrus* (pinhole borer), against representatives of the sub-class of the Siricidae, such as, for example, Paururus spp. (Sirex species), against representatives of the sub-class of the Bostrychidae, such as, for example, *Bostrychus capucinus,* and against representatives of the sub-class of the Lyctidae, such as, for example, *Lyctus brunneus* (brown powder-post beetle).

The mixing ratios of the individual components in the combinations according to the invention can vary within wide limits. For practical reasons, however, ratios by weight of the components and ammonium salts of between 20:1 and 1:5000, preferably 10:1 and 1:1000, particularly preferably 10:1 and 1:25, will be selected. For the component silafluofen, the ratio to the ammonium salts is preferably between 1:1 and 1:1000, particularly preferably between 1:2 and 1:500 (silafluofen: ammonium salt).

The compositions according to the invention can be marketed in the customary preparations known to the expert. They can be formulated in a variety of ways, as predetermined by the biological and/or chemico-physical parameters. The following possibilities are therefore suitable for formulation:

Wettable powders (WP), emulsifiable concentrates (EC), aqueous solutions (SC), emulsions, sprayable solutions, oil- or water-based dispersions (SC), oil formulations, suspo-emulsions (SC), dusts (DP), seed-dressing products, granules in the form of microgranules, spray granules, coated granules and adsorption granules, water-dispersible granules (WG), (EW), ULV formulations, microcapsules, waxes or baits.

These individual types of formulation are known in principle and are described, for example, in Winnacker-Küchler, "Chemische Technologie [Chemical Technology]", Volume 7, C. Hauser Verlag Munich, 4th Ed., 1986; van Falkenburg, "Pesticides Formulations", Marcel Dekker N.Y., 2nd Ed. 1972–73; K. Martens, "Spray Drying Handbook", 3rd Ed. 1979, G. Goodwin Ltd. London.

The formulation auxiliaries required, such as inert materials, surfactants, solvents and other additives, are equally known and described, for example, in: Watkins, "Handbook of Insecticide Dust Diluents and Carriers", 2nd Ed., Darland Books, Caldwell N.J.; H. v.Olphen, "Introduction to Clay Colloid Chemistry", 2nd Ed., J. Wiley & Sons, N.Y.; Marsden, "Solvents Guide",2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzfl ächenaktive Äthylenoxidaddukte [Surface-Active Ethylene Oxide Adducts]", Wiss. Verlagsgesell., Stuttgart 1976; Winnacker-Küchler, "Chemische Technologie [Chemical Technology]", Volume 7, C. Hauser Verlag Munich, 4th Ed. 1986.

Emulsifiable concentrates are prepared by dissolving the active substance in an organic solvent, for example butanol, cyclohexanone, dimethylformamide, xylene or else higher-boiling aromatics or hydrocarbons, with an addition of one or more emulsifiers. The following can be used as emulsifiers: calcium salts of an alkyllauryl-sulfonic acid, such as calcium dodecylbenzenesulfonate, or non-ionic emulsifiers, such as fatty acid polyglycol esters, alkyllauryl polyglycol ethers, fatty alcohol polyglycol ethers, propylene oxide/ ethylene oxide condensation products, alkyl polyethers, sorbitan fatty acid esters, polyoxyethylene sorbitan fatty acid esters or polyoxyethylene sorbitol esters.

Wettable powders are preparations which are uniformly dispersible in water and which, besides the active substance and a diluent or inert substance, also contain wetting agents, for example polyoxethylated alkylphenols, polyoxethylated fatty alcohols, alkylsulfonates or alkylphenolsulfonates, and dispersing agents, for example sodium lignosulfonate, sodium 2,2'-dinaphthylmethane-6,6'-disulfonate, sodium dibutylnaphthalenesulfonate, or else sodium oleylmethyltauride.

Emulsifiable concentrates are prepared by dissolving the active substance in an organic solvent, for example butanol, cyclohexanone, dimethylformamide, xylene or else higher-boiling aromatics or hydrocarbons, with an addition of one or more emulsifiers. The following can be used as emulsifiers: calcium salts of an alkylaryl-sulfonic acid, such as calcium dodecylbenzenesulfonate, or non-ionic emulsifiers, such as fatty acid polyglycol esters, alkylaryl polyglycol ethers, fatty alcohol polyglycol ethers, propylene oxide/ ethylene oxide condensation products, alkyl polyethers, sorbitan fatty acid esters, polyoxyethylene sorbitan fatty acid esters or polyoxyethylene sorbitol esters.

Dusts are obtained by grinding the active substance with finely divided solid substances, for example talc, natural clays such as kaolin, bentonite, pyrophyllite or diatomaceous earth. Granules can be produced either by spraying the active substance onto adsorptive, granulated inert material, or by applying active substance concentrates onto the surface of carriers, such as sand, kaolinites or granulated inert material, by means of binders, for example polyvinyl alcohol, sodium polyacrylate or, alternatively, mineral oils. Suitable active substances can also be granulated in a manner which is conventional for the production of fertilizer granules, if desired in a mixture with fertilizers.

The concentration of active substance in wettable powders is, for example, approximately 10 to 90% by weight; the remainder to 100% by weight is composed of customary formulation components. In the case of emulsifiable concentrates, the concentration of active substance can be about 5 to 80% by weight. Formulations in the form of dusts usually contain 5 to 20% by weight of active substance, sprayable solutions approximately 2 to 20% by weight. In the case of granules, the active substance content depends partly on whether the active compound is in liquid or solid form and on which granulation auxiliaries, fillers etc. are used.

In addition, the active substance formulations mentioned contain, if appropriate, the adhesives, wetting agents, dispersants, emulsifiers, penetrants, solvents, fillers or carriers which are conventional in each case.

Inert substances which can be used are, in particular, n-butyl glycolate, polyglycol ether or dipropylene glycol monoethyl ether.

For use, the concentrates, which are in commercially available form, are, if appropriate, diluted in the customary manner, for example using water in the case of wettable powders, emulsifiable concentrates, dispersions and, in some cases, also in the case of microgranules. Preparations in the form of dusts or granulated preparations and also sprayable solutions and oil formulations which are bought ready to use are usually not further diluted with other inert substances prior to use.

The compositions according to the invention are preferably marketed in the form of concentrates which can be diluted with water or as ready-to-use solutions. The active substance combinations according to the invention in the formulated compositions amount, for example, to 0.1 to 80% by weight.

In the case of insecticidal compositions, the concentrations of the active substances in the commercial formulations may vary. In the case of emulsifiable concentrates, the concentration of active substance amounts to approximately 1 to 50%.

The application rate of active substance required varies with the external conditions, such as temperature, humidity, and the field of application, for example for the treatment of wood, soil or plants. The application rate can vary within wide limits:

1) in the treatment of wood, between 0.00001 $g/m^2$ and 10 $g/m^2$.

2) in the treatment of the soil, between 0.0001 $g/m^2$ and 100 $g/m^2$.

3) in the treatment of plants, between 1 g/ha and 1000 g/ha.

The use concentration can vary between 0.1 ppm (≙0.0001 g/ 1) and 10000 ppm (≙10 g/l), preferably between 0.5 and 5000 ppm.

A combination of the active substances means that the insecticidal active substances are applied together or, in the case of a so-called split application, one after the other, with a few days' interval.

If required, the compositions according to the invention can be combined with other active substances, preferably with fungicides and other insecticides. Unless otherwise specified, percentages are % by weight. The invention is illustrated by the example which follows, without limiting it thereto:

EXAMPLE 1

Effect of the compositions according to the invention against wood-destroying termites.

The test insect used was Reticulitermes speratus. Workers together with a filter paper substrate, which had been immersed for 5 seconds in a solution containing the composition in question, were placed into a glass container at 27° C. Five animals were used for each repetition. Each batch was repeated 2–4 times. The number of surviving animals was determined 1 day after the application The same result, or better results, than with the individual components can be achieved using considerably lower amounts of the combinations according to the invention.

TABLE 1

Insecticidal effect of the combinations according to the invention on Reticulitermes speratus.

| Compound | Conc. (ppm of a.i.) | % effect |
| --- | --- | --- |
| Alkylbenzyldimethyl- | 10 | 0 |
| ammonium chloride | 1000 | 80 |
| (A1) | 5000 | 100 |
| Silafluofen | 2.5 | 30 |
| Imidacloprid | 25 | 30 |
| Tralomethrin | 0.5 | 20 |
| Permethrin | 2.5 | 60 |
| Silafluofen + A1 | 2.5 + 10 | 100 |
|  | 2.5 + 1000 | 100 |
| Imidacloprid + A1 | 25 + 10 | 30 |
|  | 25 + 1000 | 100 |
|  | 25 + 5000 | 100 |
| Tralomethrin + A1 | 0.5 + 10 | 50 |
|  | 0.5 + 1000 | 70 |
|  | 0.5 + 5000 | 100 |
| Permethrin + A1 | 2.5 + 10 | 50 |
|  | 2.5 + 1000 | 100 |
|  | 2.5 + 5000 | 100 |

We claim:

1. An insecticidal composition comprising synergistic insecticidally effective amounts of $C_8$–$C_{18}$ alkyl benzyldimethyl ammonium chloride, and silafluofen, wherein the silafluofen and the ammonium salt are present in a ratio by weight of 20:1 to 1:10,000.

2. The insecticidal composition of claim 1, wherein the ratio by weight is 20:1 to 1:5000.

3. The insecticidal composition of claim 1, which comprises 0.1 to 50% by weight of the active insecticidal mixture and 99.5–50% by weight of customary formulation auxiliaries for preparations in the form of sprayable solutions.

4. A method of controlling insects, which comprises applying a synergistic insecticidally effective amount of the composition of claim 1 to the insects or their wood, soil or plant habitats.

5. The method of claim 4, wherein an application rate of 15 to 600 l of the synergistic mixtures is applied per $m^3$ of wood.

6. The method of claim 4, wherein spray mixtures are applied which contain 0.001 to 1000 g/l of the active insecticidal combination.

7. The method of claim 4, wherein the active insecticidal ingredients are applied together or one shortly after the other.

* * * * *